United States Patent
Nomura et al.

(10) Patent No.: US 10,905,384 B2
(45) Date of Patent: Feb. 2, 2021

(54) MONITOR

(71) Applicant: NIHON KOHDEN CORPORATION, Tokyo (JP)

(72) Inventors: Ei Nomura, Tokyo (JP); Masami Tanishima, Tokyo (JP); Hiroko Hagiwara, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1271 days.

(21) Appl. No.: 13/933,480

(22) Filed: Jul. 2, 2013

(65) Prior Publication Data

US 2014/0012096 A1 Jan. 9, 2014

(30) Foreign Application Priority Data

Jul. 9, 2012 (JP) .................................. 2012-153740

(51) Int. Cl.
*A61B 5/00* (2006.01)
*A61B 5/0205* (2006.01)
(Continued)

(52) U.S. Cl.
CPC ................ *A61B 5/746* (2013.01); *A61B 5/01* (2013.01); *A61B 5/02055* (2013.01);
(Continued)

(58) Field of Classification Search
CPC ..... A61B 5/746; A61B 5/742; A61B 5/02055; A61B 5/14542; A61B 5/031; A61B 5/01; A61B 5/0476
(Continued)

(56) References Cited

U.S. PATENT DOCUMENTS 8,031,076 B2 10/2011 Sachanandani
2006/0025698 A1 2/2006 Nakagawa et al.
(Continued)

FOREIGN PATENT DOCUMENTS

EP 2 314 211 A1 4/2011
JP 56-63335 A 5/1981
(Continued)

OTHER PUBLICATIONS

Japanese Office Action for the related Japanese Patent Application No. 2012-153740 dated Oct. 6, 2015.
(Continued)

*Primary Examiner* — Gary Jackson
*Assistant Examiner* — Sebastian X Lukjan
(74) *Attorney, Agent, or Firm* — Pearne & Gordon LLP (57) ABSTRACT

Herein disclosed is a monitor, including: a measurement section that acquires measured values of a plurality of parameters showing a health state of a living body; a classification setting section that classifies a relationship among the measured values of the plurality of parameters into a plurality of types of detection states; a status setting section that respectively assigns any of a plurality of types of alarm statuses to the plurality of types of detection states; a state specifying section that specifies one of the plurality of types of detection states on the basis of the measured values acquired by the measurement section; and an annunciation section that outputs an alarm corresponding to the alarm status assigned to the specified detection state.

11 Claims, 6 Drawing Sheets

(51) Int. Cl.
    A61B 5/145    (2006.01)
    A61B 5/03     (2006.01)
    A61B 5/01     (2006.01)
    A61B 5/0476   (2006.01)
    G16H 40/63    (2018.01)
    G16H 50/30    (2018.01)
    G16H 50/20    (2018.01)
    G16H 50/70    (2018.01)
    G06F 19/00    (2018.01)

(52) U.S. Cl.
    CPC ............ *A61B 5/031* (2013.01); *A61B 5/0476* (2013.01); *A61B 5/14542* (2013.01); *A61B 5/742* (2013.01); *G06F 19/00* (2013.01); *G16H 40/63* (2018.01); *G16H 50/20* (2018.01); *G16H 50/30* (2018.01); *G16H 50/70* (2018.01)

(58) Field of Classification Search
    USPC ........................................................ 600/301
    See application file for complete search history.

(56) References Cited

U.S. PATENT DOCUMENTS

| | | | |
|---|---|---|---|
| 2008/0188733 A1* | 8/2008 | Al-Ali | A61B 5/0205 600/364 |
| 2009/0131757 A1* | 5/2009 | Jayaram | A61B 5/0205 600/300 |
| 2010/0016682 A1 | 1/2010 | Schluess et al. | |
| 2010/0069725 A1 | 3/2010 | Al-Ali | |
| 2010/0099964 A1 | 4/2010 | O'Reilly et al. | |
| 2011/0080294 A1 | 4/2011 | Tanishima et al. | |
| 2011/0098540 A1* | 4/2011 | Tanishima | A61B 5/0205 600/300 |
| 2011/0234597 A1* | 9/2011 | Kohut | G06T 11/206 345/440 |
| 2012/0029314 A1* | 2/2012 | Paquet | A61B 5/02055 600/301 |
| 2012/0226117 A1* | 9/2012 | Lamego | A61B 5/14532 600/316 |
| 2012/0286955 A1* | 11/2012 | Welch | A61B 5/746 340/573.1 |
| 2015/0094546 A1 | 4/2015 | Al-Ali | |
| 2015/0245773 A1 | 9/2015 | Lamego | |

FOREIGN PATENT DOCUMENTS

| | | |
|---|---|---|
| JP | 2010-512925 A | 4/2010 |
| JP | 2011-78562 A | 4/2011 |
| JP | 2012-85906 A | 5/2012 |
| WO | 2008/075288 A2 | 6/2008 |
| WO | 2010-031070 A2 | 3/2010 |
| WO | WO-2010144961 A1 * | 12/2010 ........... A61B 5/0205 |
| WO | 2011-081597 A1 | 7/2011 |
| WO | 2012/075322 A2 | 6/2012 |

OTHER PUBLICATIONS

Notification of First Office Action issued in Chinese Patent Application No. 201310275070 dated Jul. 4, 2016.
Chinese Office Action issued in Patent Application No. CN 201310275070 dated Mar. 3, 2017.
Extended European Search Report issued in Patent Application No. EP 13 17 4704 dated Mar. 9, 2017.
Chinese Office action issued in Patent Application No. CN 201310275070.3 dated Sep. 26, 2017.
Summons to attend oral proceedings Patent Application No. EP 13 174 704.0 dated Jun. 18, 2018.
Reply to Communication Under Article 94(3) EPC dated May 9, 2018.
Chinese Office Action issued in Patent Application No. CN 201310275070.3 dated May 18, 2018.
European Office Action issued in Patent Application No. EP 13 174 704 dated Jan. 2, 2018.
Letter of Reply of the Applicant to the European Search Report and Acknowledgement of Receipt dated Oct. 11, 2017.

* cited by examiner

MONITOR

BACKGROUND OF THE INVENTION

The invention relates to a monitor with an annunciating section that acquires a measured value of a parameter representing a state of a living body and that outputs an alarm when the measured value fulfills a predetermined condition.

A known apparatus of this type defines a plurality of types of alarm statuses on a per-parameter-basis and annunciates any of the plurality of types of alarm statuses on the basis of the thus-acquired measured value of the parameter (see; for instance, Patent Document 1). Here, the alarm status is an indicator that represents an emergence response according to a risk level of a symptom. A high priority (Crisis), a middle priority (Warning), and a low priority (Advisory) are named as examples of the alarm status.

For instance, in a neonatal intensive care unit (NICU), a low birth weight infant (a weight of less than 2500 grams) undergoes apnea (apnea of prematurity) with great frequency for reasons of immaturity of a respiratory center that is frequently fraught with hypoxia and bradycardia. They might bring on disabilities in a brain that is in the course of development or impair functions of internal organs, which may seriously affect a life or bring on long-term serious prognostic influence. Therefore, in order to monitor emergence of hypoxia and bradycardia and enable performance of a prompt, appropriate response, measuring arterial oxygen saturation (SpO2) and a heart rate is important. Alarm statuses employed at this time include; for instance, a middle priority is given to a case where a lower limit value of SpO2 falls below 85% that indicates hypoxia, whilst a high priority is given to a case where the lower limit value falls below 75% that suggests hypercyanosis (profound anoxemia). Further, a middle priority is also given to a case when the lower limit value of the heart rate falls below 100 bpm that suggests slight bradycardia, whereas a high priority is given to a case where the lower limit value falls below 80 bpm that suggests high bradycardia.

[Patent Document 1] JP-2011-78562

A symptom called "hypoxic bradycardia" that shows a reduction in heart rate in a hypoxic state requires a high-priority response. The symptom is defined as a state in which the lower limit value of SpO2 falls below 85% and in which the lower limit value of the heart rate falls below 100 bpm. However, in relation to the defined alarm status of each of the parameters, both SpO2 and the heart rate correspond to the middle priority. For this reason, if monitoring depends solely on an annunciated alarm status, a delay will arise in finding hypoxic bradycardia, or the symptom will be considered as a transient symptom despite the fact that hypoxic bradycardia which requires high priority response is in reality under development.

SUMMARY

This invention provides a monitor enabling a healthcare worker to take a response appropriate for an emergency even in a case of a symptom in which a plurality of parameters showing a health state of a living body are relevant to each other.

It is therefore an aspect of the invention to provide a monitor comprising:

a measurement section configured to acquire measured values of a plurality of parameters indicating a health state of a living body;

a classification setting section configured to classify a relationship among the measured values of the plurality of parameters into a plurality of types of detection states;

a status setting section configured to respectively assign any of a plurality of types of alarm statuses to the plurality of types of detection states;

a state specifying section configured to specify one of the plurality of types of detection states on the basis of the measured values acquired by the measurement section; and an annunciation section configured to output an alarm corresponding to the alarm status assigned to the specified detection state.

By means of such a configuration, an alarm status appropriate for a health state of the living body can be assigned on the basis of a relationship between measured values of a plurality of parameters acquired by the measurement section. Even in a state in which a symptom will be difficult to detect if a priority is determined on the basis of only an alarm status set for each of the parameters, a quick response to a symptom and a treatment appropriate for the symptom can be taken because appropriate alarm statuses can be assigned.

The monitor may further comprise:

a display section; and a display control section configured to display on the display section a coordinate system formed from a plurality of coordinate axes assigned to the plurality of parameters, wherein assignment of the alarm statuses is carried out by use of the coordinate system.

By means of such a configuration, a relationship among measured values of a plurality of parameters become obvious at a glance. Therefore, a domain in a coordinate system corresponding to a detection state that needs alarm status setting or a correction is intuitively grasped, and setting and correction work can be smoothly performed.

The display control section may be configured to display at least one of indices corresponding to the measured values in the coordinate system.

By means of such a configuration, a current health state of the living body can be intuitively grasped by means of a positional relationship between the domains assigned predetermined alarm statuses.

The display control section may be configured to change at least one of a color, brightness, and a shape of the index according to a time when the measurement section acquired the measured value.

By means of the configuration, a shift in the health state of the living body can be intuitively grasped by means of the positional relationship between the domains assigned the predetermined alarm statuses.

The monitor may further comprise a data specifying section configured to specify at least one of the indices, wherein the display control section is configured to cause the display section to display a moment-to-moment change in the measured value so as to include a time when the measurement section acquired the measured value corresponding to an index specified by the data specifying section.

By means of the configuration, a worrisome index is specified on the index display screen that inevitably displays measured values which are chronologically discrete, whereby measured values that are chronologically continual before and after the measured value can be displayed. A more detailed examination of the measured data becomes possible. Further, specifying the index can be carried out on the basis of a positional relationship between the index and the domain assigned the predetermined alarm status. Hence, measurement data can be intuitively and efficiently checked.

Requirements for demarcation among the plurality of types of classified detection states may be made variable by the classification setting section.

By means of the configuration, it is possible to set alarm statuses appropriate for an individual difference of the living body that is a monitoring target.

The plurality of types of detection states may be classified according to a threshold value set for each of the plurality of parameters. The plurality of types of detection states may be classified according to a ratio of measured values of the plurality of parameters. The plurality of types of detection states may be classified according to a relationship curve between measured values of the plurality of parameters.

The plurality of types of alarm statuses may include a high priority (Crisis), a middle priority (Warning), a low priority (Advisory), and a non-alarm status.

The plurality of parameters may be able be selected from a parameter group including a cardiac rate, a frequency of pulse, arterial oxygen saturation, oxyecoia partial pressure, carbon dioxide partial pressure, a concentration of carbon dioxide at end-expiration, a concentration of inspired carbon dioxide, blood pressure, a breathing rate, brain pressure, body heat, an ST value, Apnea (a period of cessation of respiration), FiO2 (an expiratory oxygen concentration), an amount of circulating blood, a cardiac output, a BIS value (a bispectral index), a concentration of anesthetic gas, a vent airflow, an expiratory airflow, a SV (single stroke volume), SVV (a coefficient of fluctuation in single stroke volume), PPV (a coefficient of fluctuation in pulse pressure), SPV (coefficient of fluctuation in blood pressure in contraction stage), and PI (pulse rate).

It is another aspect of the invention to provide a monitor comprising:

a measurement section configured to acquire a measured value of a first parameter and a measured value of a second parameter that represent a health state of a living body;

a classification setting section configured to classify a relationship between a measured value of the first parameter and a measured value of the second parameter into a plurality of types of detection states by means of at least one threshold value pertinent to the first parameter and at least one threshold value pertinent to the second parameter;

a status setting section configured to assign any of the plurality of types of alarm statues respectively to the plurality of types of detection states;

a status specifying section configured to specify one of the plurality of types of detection states according to the measured value acquired by the measurement section;

an annunciation section configured to output an alarm corresponding to an alarm status assigned to the specified detection state;

a display section;

a display control section configured to cause the display section to display a coordinate plane formed from coordinate axes assigned to the first parameter and the second parameter, wherein assignment of the alarm statuses is configured to be carried out by use of the coordinate plane.

By means of the configuration, an alarm status appropriate for a health state of the living body can be assigned on the basis of a relationship between two measured values acquired by the measurement section. Even in a state in which a symptom will be difficult to detect if a priority is determined on the basis of only an alarm status set for each of the parameters, an appropriate alarm status can be assigned. Hence, a quick response to a symptom and a treatment appropriate for the symptom can be taken. In particular, assignment of alarm statuses are carried out with reference to threshold values of the respective parameters by use of the coordinate plane, and hence significant classification can be set through intuitive operation.

DETAILED DESCRIPTION OF EMBODIMENTS

An embodiment of the invention is hereunder described in detail by reference to the accompanying drawings.

Figure 1:
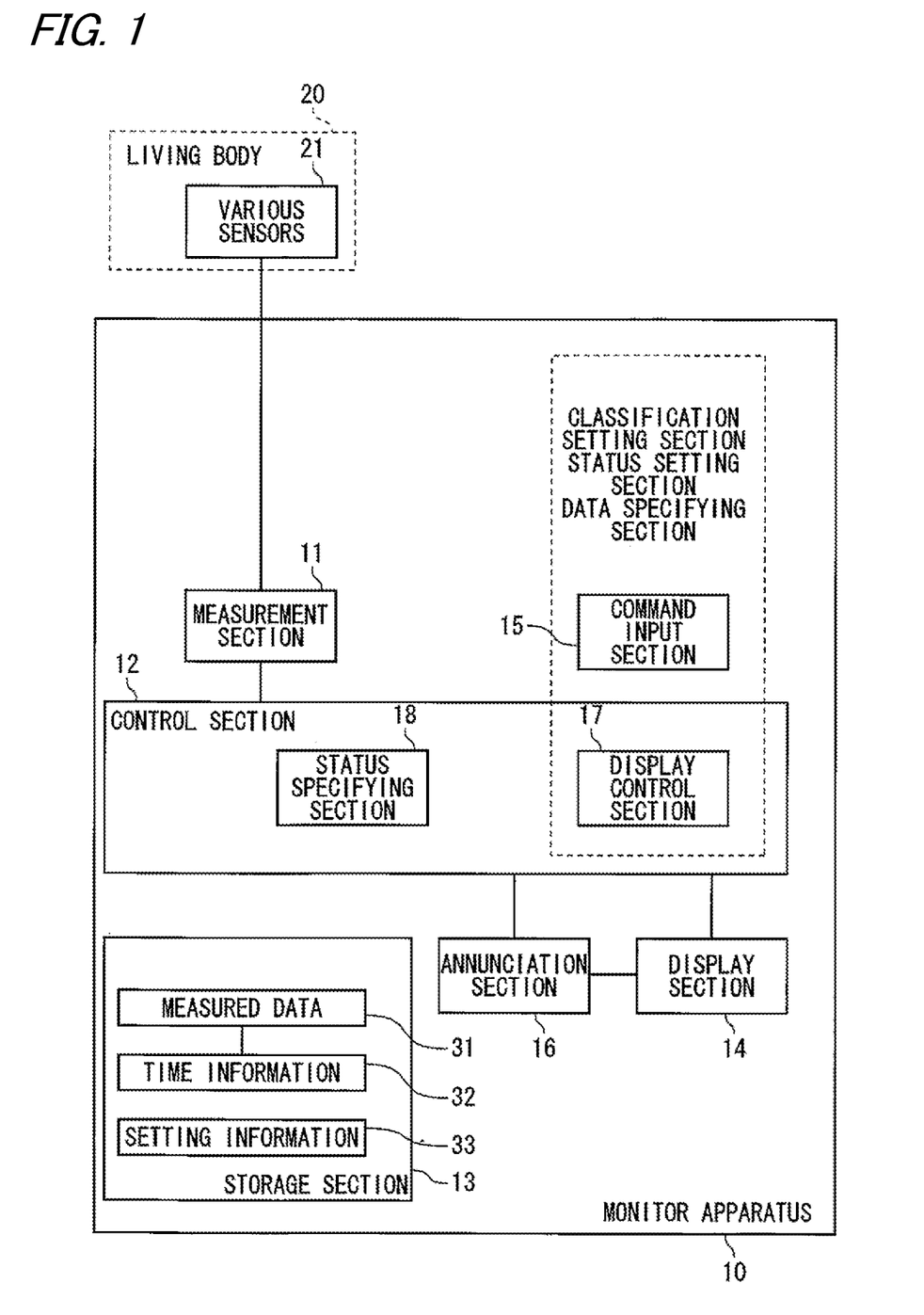
FIG. 1 is a functional block diagram showing a configuration of a monitor according to an embodiment of the invention.

FIG. 1 is a functional block diagram showing a configuration of a monitor 10 of an embodiment of the invention. The monitor 10 is equipped with a measurement section 11, a control section 12, a storage section 13, a display section 14, a command input section 15, and an annunciation section 16.

A living body 20 wears various sensors 21, such as electrodes and cuffs, and measured signals pertinent to a plurality of parameters showing a health state of the living body 20 are input to the measurement section 11. The measurement section 11 acquires the measured values of the parameters. In the following descriptions, explanations are given to a case where a measured value of a heart rate and a measured value of arterial oxygen saturation are acquired as a plurality of parameters.

The control section 12 is an arithmetic processing circuit equipped with an arithmetic processing element, like a CPU, and memory, like RAM and ROM, and controls entire operation of the monitor 10. Various operations and functions of the control section 12 to be described below can be implemented by means of operation of hardware, such as a circuitry element, operation of software like a program stored in the arithmetic processing element, or a combination thereof.

The storage section 13 is connected in a communicable way with the control section 12. At least some of the measured values acquired by the measurement section 11 are stored as measurement data 31 in the storage section 13 by way of the control section 12. The respective pieces of measurement data 31 are stored in association with time information 32 that shows measured times.

The display section 14 is a display provided on a front side of the monitor. The display section 14 is connected in a communicable way to the control section 12. The control section 12 has a display control section 17 as a functional element. The display control section 17 displays in real time on the display section 14 a measured signal input to the measurement section 11.

The command input section 15 is connected in a communicable way to the control section 12. The command input section 15 is configured as a man-machine interface by way of which the user inputs a command and made up of buttons, switches, a mouse, a keyboard, and others. At least a portion of the display section 14 can also be configured as a touch panel or so as to act as a portion of the command input section 15.

The annunciation section 16 is connected in a communicable way to the control section 12. The control section 12 has a status specifying section 18 as a functional element. When determining that the living body 20 to be monitored is in a predetermined health state, the status specifying section 18 outputs an alarm to the annunciation section 16. An alarm status representing response emergency is previously defined in connection with each of predetermined health states. The annunciation section 16 outputs an alarm assigned an alarm status, thereby annunciating an emergency to a user.

The alarm output is carried out in at least one of a visual way (a message display, a mark display, light emission, and the like) and an audible way (a beep sound, an announcement, and the like). The annunciation section 16 is connected in a communicable way to the display section 14. The display control section 17 outputs at least some of visual alarms by utilization of the display section 14.

A method for setting an alarm status is now described. When a command for effecting a shift to an alarm status setting mode is issued by way of the command input section 11, the display control section 17 causes the display section 14 to display a status setting screen 40 shown in FIG. 2A.

Figure 2A:
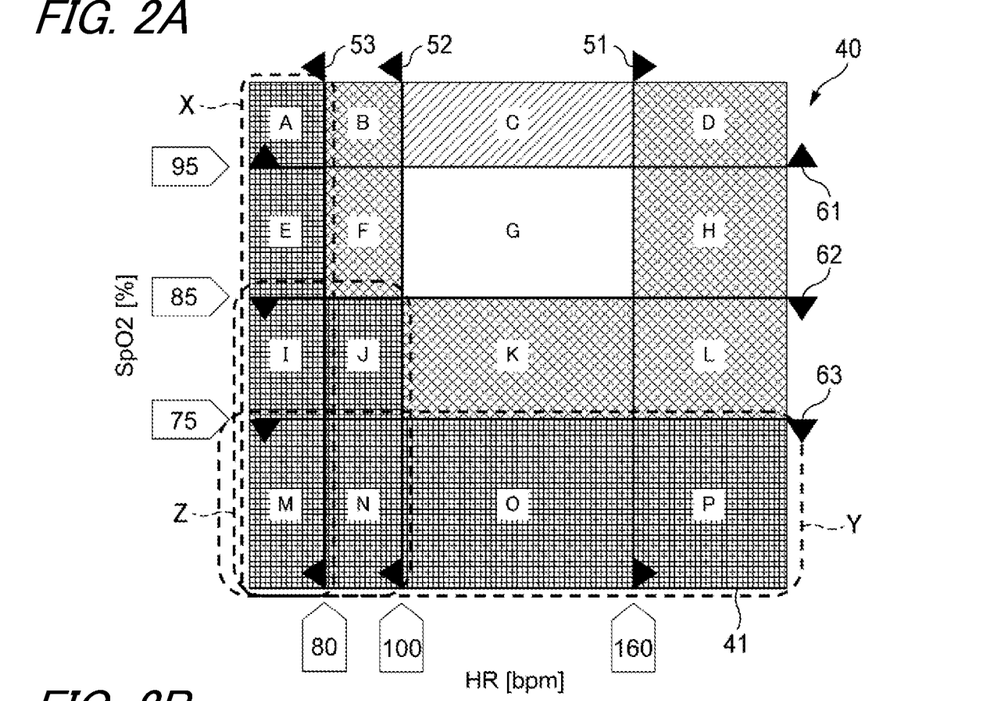
FIGS. 2A and 2B are diagrams showing an example of an alarm status setting screen and a measured value display screen that are displayed in a display section of the monitor.

The status setting screen 40 includes a coordinate plane 41 including a horizontal axis assigned to a heart rate (hereinafter abbreviated as "HR") and a vertical axis assigned to arterial oxygen saturation (hereinafter indicated as SpO2). First to third threshold setting lines 51, 52, and 53 that extend in a direction orthogonal to the horizontal axis and fourth to sixth threshold setting lines 61, 62, and 63 that extend in a direction orthogonal to the vertical axis are displayed on the coordinate plane 41. As a result of the first to third threshold value setting lines 51, 52, and 53 crossing the fourth to sixth threshold value setting lines 61, 62, and 63, a total of 16 domains A to P are defined on the coordinate plane 41.

The first threshold value setting line 51 is for setting a threshold value of a maximum HR value and set to 160 bpm in the illustrated example. When a measured HR value is the threshold value or more, a fast pulse is suspected in a monitoring target, and hence an alarm status of the threshold value of the maximum HR value is given a middle priority (Warning).

The second threshold value setting line 52 is for setting a first threshold value of a minimum HR value and set to 100 bmp in the illustrated example. When the measured HR value is the threshold value or less, slight bradycardia is suspected in the monitoring target, and hence an alarm status of the first threshold value of the minimum HR value is given a middle priority.

The third threshold value setting line 53 is for setting a second threshold value of the minimum HR value and set to 80 bmp in the illustrated example. When the measured HR value is the threshold value or less, profound bradycardia is suspected in the monitoring target, and hence an alarm status of the second threshold value of the minimum HR value is given a high priority (Crisis).

When the measured HR value falls within a range between the first threshold value setting line 51 and the second threshold value setting line 52, the health state of the monitoring target is deemed as being normal, and an alarm status of this case is taken as a non-alarm status.

The fourth threshold value setting line 61 is for setting a threshold value of a maximum SpO2 value and set to 95% in the illustrated example. When a measured SpO2 value is the threshold value or more, retinopathy of prematurity attributable to hyperoxemia is suspected in a monitoring target, and hence an alarm status of the threshold value of the maximum SpO2 value is given a low priority (Advisory).

The fifth threshold value setting line 62 is for setting a first threshold value of a minimum SpO2 value and set to 85% in the illustrated example. When the measured HR value is the threshold value or less, hypoxia is suspected in the monitoring target, and hence an alarm status of the first threshold value of the minimum SpO2 value is given a middle priority.

The sixth threshold value setting line 63 is for setting a second threshold value of the minimum SpO2 value and set to 75% in the illustrated example. When the measured SpO2 value is the threshold value or less, hypercyanosis is suspected in the monitoring target, and hence an alarm status of the second threshold value of the minimum SpO2 value is given a high priority.

When the measured SpO2 value falls within a range between the fourth threshold value setting line 61 and the fifth threshold value setting line 62, the health state of the monitoring target is deemed as being normal, and an alarm status of this case is taken as a non-alarm status.

In the embodiment, in addition to setting alarm statuses appropriate for measured values of the respective parameters, relationships among the plurality of measured values of the parameters are sorted into a plurality of types of detection states. The alarm statuses are assigned to the plurality of types of detection states, respectively.

As mentioned above, the coordinate plane 41 is segmented into the 16 domains A to P by means of the six threshold value setting lines 51 to 53 and 61 to 63. Since a range of each of the domains is specified as coordinates involving measured HR values and measured SpO2 values, the range can be deemed as a detection state based on a relationship between HR and SpO2. Put another way, the plurality of types of detection states are sorted according to the threshold values defined in connection with HR and SpO2. Each of the domains is assigned any of the alarm statuses (the high priority, the middle priority, the low priority, and the non-alarm).

For instance, the domains A, E, I, and M enclosed by broken lines X are domains where measured HR values come to the second threshold value of the minimum value or less. In the domains A, E, and I, alarm statuses of measured SpO2 values are assigned the low priority, the non-alarm status, and the middle priority. However, the alarm statuses of the measured HR values are assigned the high priority. For these reasons, the higher alarm status is prioritized, and the high priority is assigned to the domains A, E, and I.

Likewise, the domains M, N, O, and P enclosed by broken lines Y are domains where measured SpO2 values come to the second threshold value of the minimum value or less. In the domains N, O, and P, alarm statuses of measured HR values are assigned the middle priority, the non-alarm status, and the middle priority. However, the alarm statuses of the measured SpO2 values are assigned the high priority. For these reasons, the higher alarm status is prioritized, and the high priority is assigned to the domains N, O, and P.

Alarm status assignment is carried out by means of the display control section 17 displaying the domains in predetermined colors. In the embodiment, the high priority is displayed in red; the middle priority is displayed in yellow; the low priority is displayed in blue; and the non-alarm status is displayed in white.

The domains I, J, M, and N enclosed by broken lines Z are domains where the measured HR value comes to the first threshold value of the minimum value or less and where the measured SpO2 value comes to the first threshold value of the lower limit value or less. In this state, hypoxic bradycardia is suspected in the monitoring target, and the original high priority reaction is required. The region J is to be originally displayed in yellow because of an overlap between the domains assigned middle priority alarm statuses of HR and SpO2. However, the domain J is assigned a high priority alarm status and displayed in red.

The user assigns an alarm status for each domain by use of the command input section 15 while viewing the coordinate plane 41 of the status setting screen 40 displayed on the display section 14 by the display control section 17. Specifically, the command input section 15 and the display control section 17 act as a classification setting section and a status setting section of the invention.

For instance, the display control section 17 first displays the respective domains in colors corresponding to alarm statuses of higher priority levels in accordance with alarm statuses set for HR and SpO2, respectively. The domains B, D, F, H, and K are assigned alarm statuses of middle priority levels according to the rule and displayed in yellow. In addition, as in the case with the domain J, a domain whose priority level needs to be changed on the basis of a relationship between a plurality of parameters is specified, and a desired alarm status is assigned to the domain.

By means of the configuration, an alarm status appropriate for a health state of the monitoring target can be assigned on the basis of a relationship between measured values of a plurality of parameters acquired by the measurement section. Even in a state in which a symptom will be difficult to detect if a priority is determined on the basis of only an alarm status set for each of the parameters like, in particular, the domain J, an appropriate alarm status can be assigned. Hence, a quick response to a symptom and a treatment appropriate for the symptom can be taken.

Since an alarm status is assigned by use of the coordinate plane 41 displayed on the display section 14, a relationship among measured values of a plurality of parameters become obvious at a glance. Therefore, a domain (a detection state) that needs alarm status setting or a correction is intuitively grasped, and setting and correction work can be smoothly performed.

The control section 12 sets the thus-set alarm statuses as setting information 33 into the storage section 13. The control section 12 reads the alarm status as required, and the alarm status is used for a setup change or a reset to an initial state, which will be descried later.

Figure 2B:
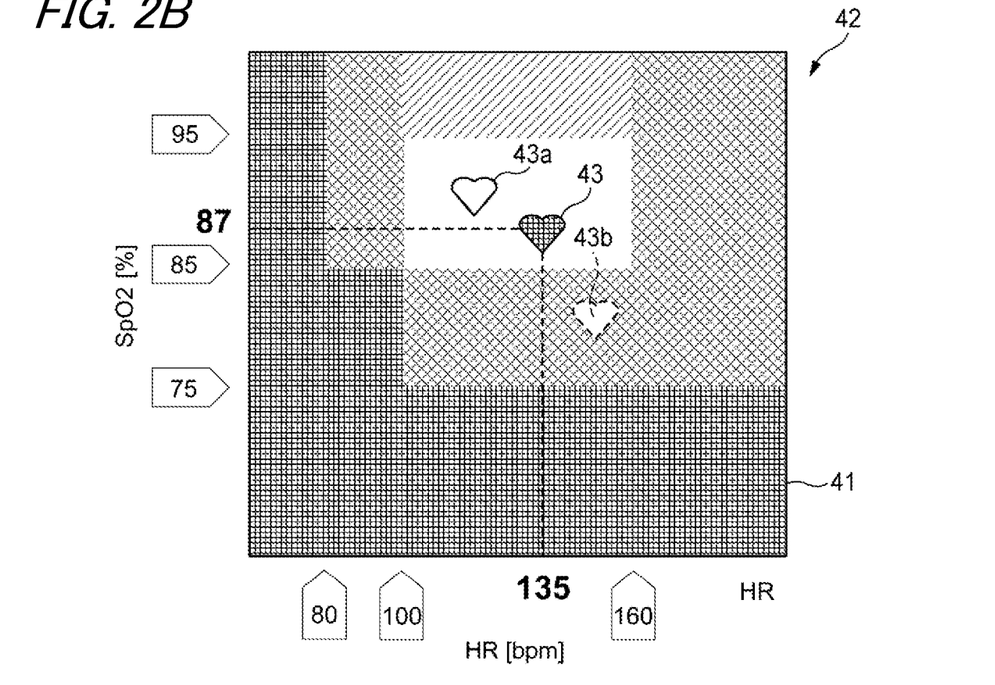

When a shift to a measurement mode is commanded by way of the command input section 15, the display control section 17 causes the display section 14 to display a measured value display screen 42, such as that shown in FIG. 2B. The first to sixth threshold value setting lines 51 to 53 and 61 to 63 are hidden in the measured value display screen 42 displayed on the display section 14, and the coordinate plane 41 separated by color according to the assigned alarm statuses is also displayed. Although omitted from the drawings, an HR measured signal waveform and an SpO2 measured signal waveform, which are input to the measurement section 11, are displayed on the display section 14 in real time.

The display control section 17 displays an index 43 corresponding to the measured value acquired by the measurement section 11 within the coordinate plane 41. FIG. 2B shows a case where a measured HR value is 135 bpm and a measured SpO2 value is 87%. The index 43 showing a current health state of the living body 20 is displayed at a point on the coordinate plane 41 where coordinates are defined by the measured values.

By means of such a configuration, the current health state of the living body 20 can be intuitively grasped by means of a positional relationship among the domains assigned the predetermined alarm statuses.

The display control section 17 is configured so as to display a plurality of indices within the coordinate plane 41 and change a color of each of the indices in accordance with a point of time when the measurement section 11 acquires a measured value. Specifically, an index 43a representing a value measured at a given time in the past is displayed, in the coordinate plane 41, in color that differs from the color of the index 43 that shows the current measured value. The value measured at a given time in the past is acquired by means of the display control section 17 reading the measurement data 31 stored in the display section 13. The display control section 17 can specify corresponding measurement data 31 by reference to the time information 32 associated with the measurement data 31.

A display mode of the index 43 based on a measurement time is not limited to a color change. In addition to or in place of the color change, at least one of brightness and shape of the index 43 can be changed.

By means of such a configuration, a shift in the health state of the living body 20 can be intuitively grasped by means of a positional relationship among the domains assigned the predetermined alarm statuses. For instance, in the case of the example shown in FIG. 2B, it is possible to obviously recognize at a glance an increase in HR and a drop in SpO2 and that the health state of the living body 20 become closer to a domain assigned the alarm state of a middle priority level.

Subsequently, when the measured HR value and the measured SpO2 value shift to a state indicated by an index 43b, the status specifying section 18 provided in the control section 12 as a functional element determines that the measured values enter the domain K shown in FIG. 2A and causes the annunciation section 16 to output a predetermined alarm corresponding to the alarm status of a middle priority level assigned to the domain.

Specifically, in accordance with the measured values acquired by the measurement section 11, the status specifying section 18 specifies one of a plurality of types of detection states corresponding to the respective domains A to P on the coordinate plane 41. The annunciation section 16 outputs an alarm corresponding to the alarm status assigned to the thus-specified detection state.

The measured value display screen 42 displayed on the display section 14 can be deemed as one mode of an alarm output from the annunciation section 16. For instance, the health state of the living body 20 indicated by the index 43 shown in FIG. 2B is normal, and an alarm, such as that output in response to the index 43b, is not output. However, this state can also be deemed as a state in which a detection state corresponding to the domain G is specified by the status specifying section 18 and in which an alarm status assigned to the state, or the non-alarm status, is being annunciated by way of the measured value display screen 42. As a result of the index 43 approaching the domain assigned the alarm status, the user can be notified of the fact that the possibility of occurrence of an alarm is now increasing. The expression "alarm output" referred to in connection with the invention is used so as to imply such a case.

The command input section 15 is arranged so as to be able to change positions of the first through sixth threshold value setting lines 51 to 53 and 61 to 63 shown in FIG. 2A. Ranges of the respective domains A to P defined on the coordinate plane 41 can thereby be changed. Put another word, requirements for a demarcation among the plurality of types of detection states corresponding to the respective divided domains A to P are changeable.

Figure 3A:
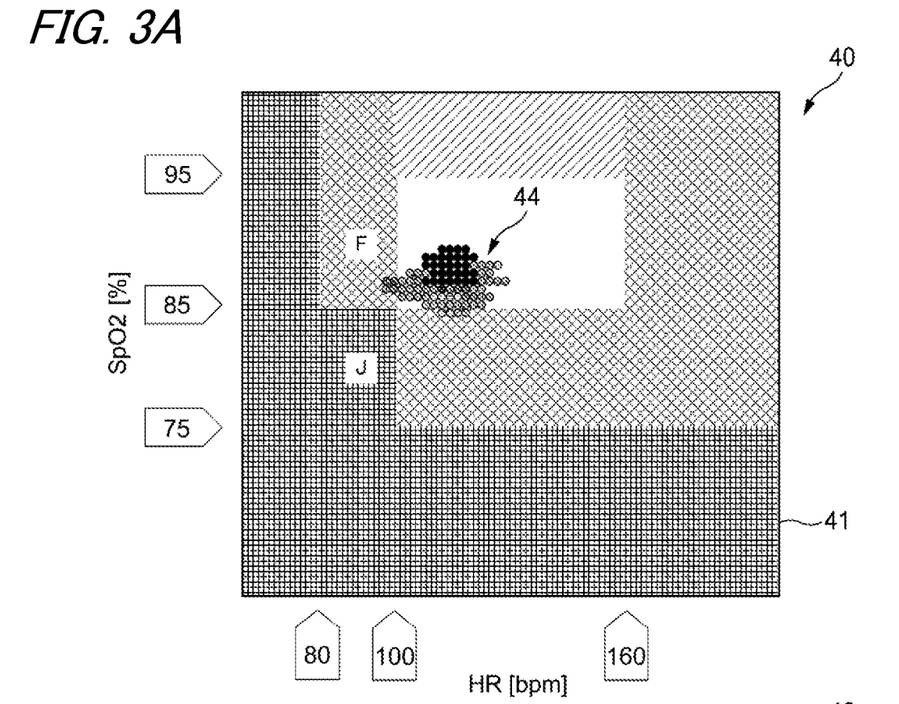
FIGS. 3A and 3B are diagrams showing another example of the alarm status setting screen to be displayed in the display section of the monitor.
Figure 3B:
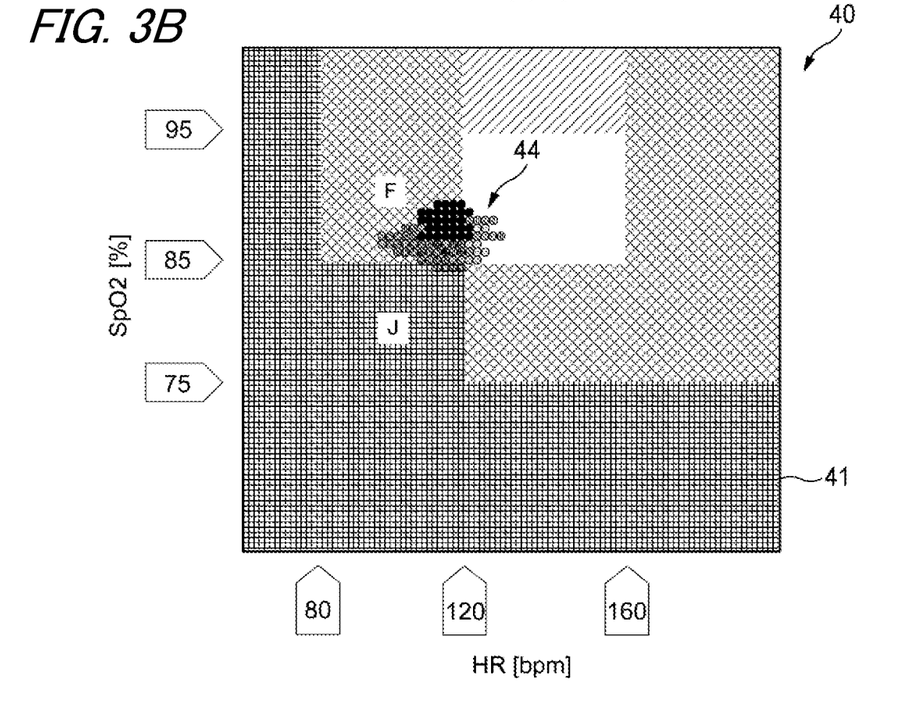

FIGS. 3A and 3B are diagrams for explaining a case where demarcation requirements are changed by use of the past measurement data 31. The display control section 17 reads a predetermined amount of measurement data 31 stored in the past in the storage section 13 and displays the thus-read measurement data in the coordinate plane 41 of the status setting screen 40 displayed on the display section 14 as shown in FIG. 3A. An index corresponding to a predetermined amount of value measured in the past forms an aggregation 44. A color of indices that form the aggregation 44 shows a time when the measured values are acquired, and newer measured values are displayed in thicker colors.

FIG. 3B shows a state in which the first threshold value of the minimum HR value indicated by the second threshold value setting line 52 is changed from 100 bpm to 120 bpm. In the state shown in FIG. 3A, a small portion of the aggregation 44 belongs to the domain F assigned the alarm status of middle priority level. However, the state shown in FIG. 3B represents that one-half or more of the aggregation 44 belongs to the domain F.

For instance, when a drop in heart rate of the living body 20 that is a monitoring target arises at a comparatively high heart rate, an alarm status of middle priority level might not be appropriately annunciated at the setting of the threshold value shown in FIG. 3A. Changing the threshold value, such as that shown in FIG. 3B, is performed in such a case, whereby the health state of the monitoring target will be appropriately annunciated. Further, the demarcation of the domain J also approaches the aggregation 44, and hence the certainty of annunciation of hypoxic bradycardia assigned a higher response priority increases.

Conversely, when an alarm is frequently annunciated despite absence of a symptom that needs a response, a conceivable countermeasure is to adjust a required threshold value so as to avoid the aggregation 44. Frequency of an unwanted alarm can be reduced, which is preferable in view of development acceleration care (developmental care).

As above, the configuration of the embodiment makes it possible to set alarm statuses appropriate for an individual difference of the living body 20 that is a monitoring target. Furthermore, the threshold values are changed by changing the ranges of the respective domains A to P according to the position of the index displayed on the coordinate plane 41. Hence, intuitive operation is possible.

The command input section 15 is configured so as to be able to specify at least one of indices included in the displayed aggregation 44. The display control section 17 is configured so as to display, on the display section 14, moment-to-moment changes in the measured value such that a measured value corresponding to the specified index includes the time when the measured value corresponding to the specified index was acquired by the measurement section 11. In other words, the command input section 15 and the display control section 17 act as a data specifying section of the invention.

Figure 4:
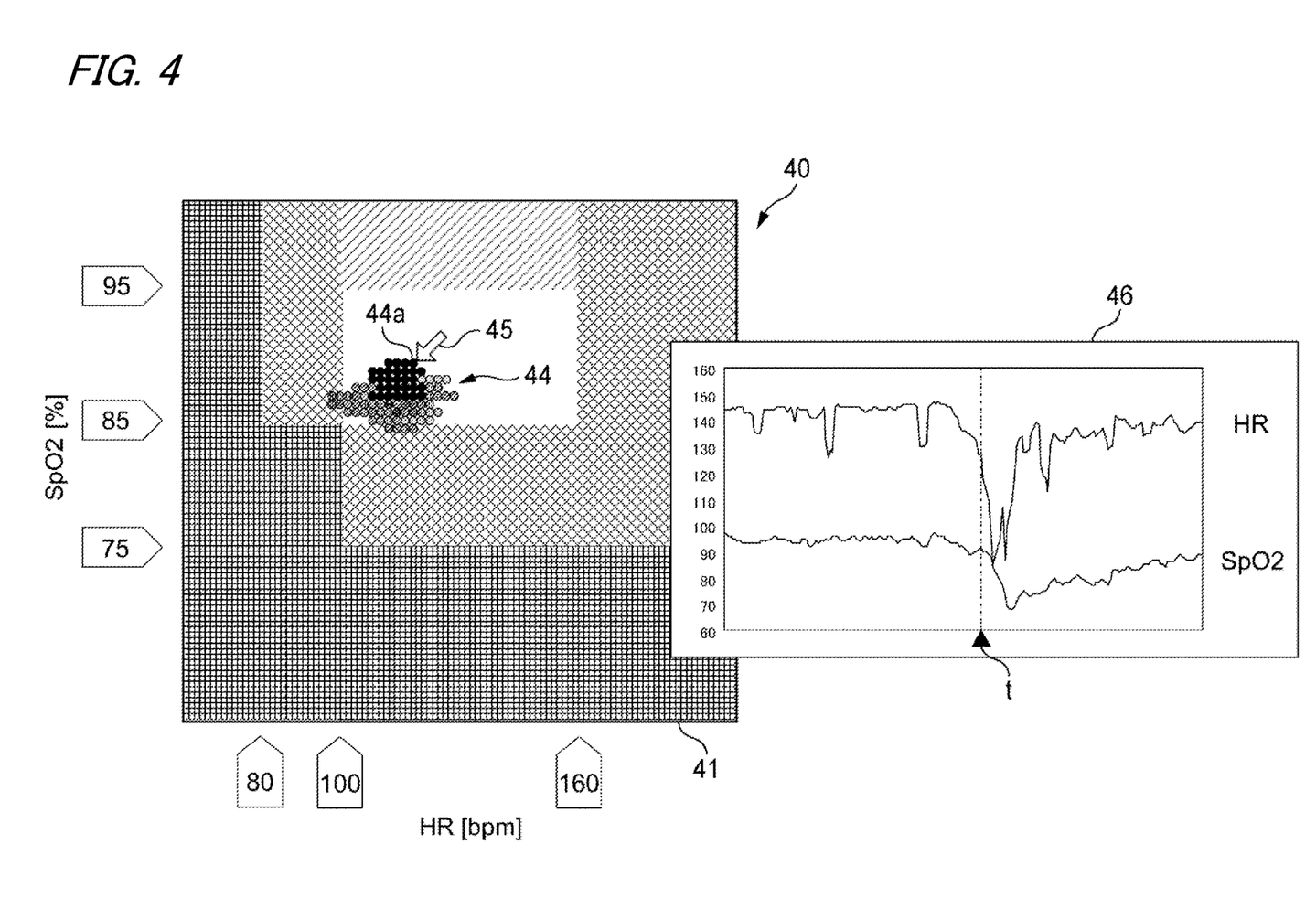
FIG. 4 is a diagram showing an example of a screen for checking a moment-to-moment change in a measured value which is displayed on the display section of the monitor.

For instance, as shown in FIG. 4, when one index 44a belonging to the aggregation 44 is specified by a cursor 45, the display section 14 displays a waveform check screen 46 that shows, as waveforms, an HR measured value and an SpO2 measured value that belong to predetermined periods around a time "t" at which the measured values corresponding to the index 44a were acquired.

Specifically, the display control section 17 refers to time information 32 stored in the storage section 13 and specifies the measurement data 31 at time "t." In addition, measurement data 31 corresponding to predetermined periods around the time "t" are specified. The display control section 17 reads the thus-specified measurement data 31 from the storage section 31, generating waveform display data and displaying the data on the waveform check screen 46.

In the configuration, a worrisome index is specified on the index display screen that inevitably displays measured values which are chronologically discrete, whereby measured values that are chronologically continual before and after the measured value can be displayed. A more detailed examination of the measured data becomes possible. Further, specifying the index can be carried out on the basis of a positional relationship between the index and the domain that is formed in the coordinate plane 41 and that corresponds to the alarm status. Hence, measurement data can be intuitively and efficiently checked.

The embodiment is intended for making the invention easy to comprehend and not for limiting the invention. It is obvious that the invention can be changed or modified without departing the gist of the invention and also include equivalents.

The parameters that represent the health state of the living body 20 and that are acquired by the measurement section 11 are not limited to a heart rate and arterial oxygen saturation. In addition to them, other parameters can also be selected so as to differ from each other from a parameter group including a frequency of pulse, oxyecoia partial pressure, carbon dioxide partial pressure, a concentration of carbon dioxide at end-expiration, a concentration of inspired carbon dioxide, blood pressure, a breathing rate, brain pressure, body heat, an ST value, Apnea (a period of cessation of respiration), FiO2 (an expiratory oxygen concentration), an amount of circulating blood, a cardiac output, a BIS value (a bispectral index), a concentration of anesthetic gas, a vent airflow, an expiratory airflow, a SV (single stroke volume), SW (a coefficient of fluctuation in single stroke volume), PPV (coefficient of fluctuation in pulse pressure), SPV (coefficient of fluctuation in blood pressure in contraction stage), and PI (pulse rate).

The horizontal axis and the vertical axis of the coordinate plane 41 are not limited to the heart rate and the arterial oxygen saturation, respectively. A parameter group consisting of parameters selected from the above are appropriately assigned to the vertical and horizontal axes.

If there are acquired measured values including a significant difference, such as a measured value of arterial oxygen saturation acquired from the right hand and a measured value of arterial oxygen saturation acquired from the left hand or a measured value of arterial oxygen saturation acquired from a superior limb and a measured value of arterial oxygen saturation acquired from an inferior limb, parameters of the same type can be deemed and selected as "plural parameters." The thus-selected parameters of the same type that provide a different meaning are assigned to the horizontal axis and the vertical axis of the coordinate plane 41, respectively.

Figure 5A:
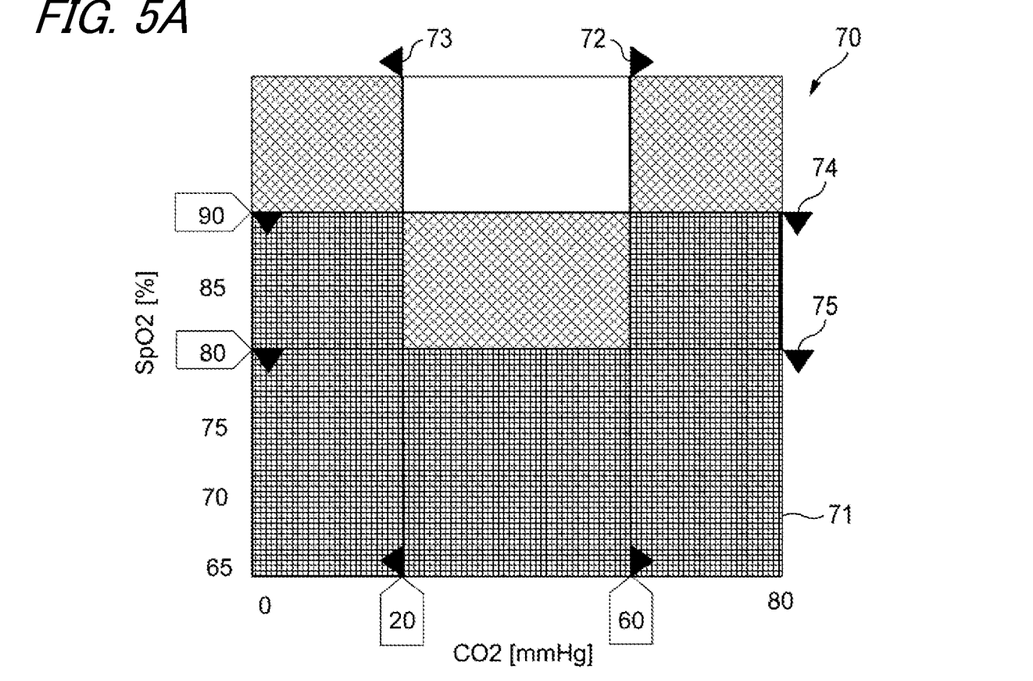
FIGS. 5A and 5B are diagrams showing still another example of the alarm status setting screen to be displayed in the display section of the monitor.

FIG. 5A shows an example of a status setting screen 70 to be displayed on the display section 14 when the concentration of carbon dioxide in aspirated air and arterial oxygen saturation are selected as a plurality of parameters. Four threshold value setting lines 72 to 75 are displayed on a coordinate plane 71 defined by a horizontal axis assigned to the concentration of carbon dioxide and a vertical axis assigned to arterial oxygen saturation. Domains assigned to a total of nine detection states are partitioned on the coordinate plane 71 as a result of crossing each other. As in the case with the embodiment, alarm statues are assigned to the respective domains and displayed in predetermined colors.

Figure 5B:
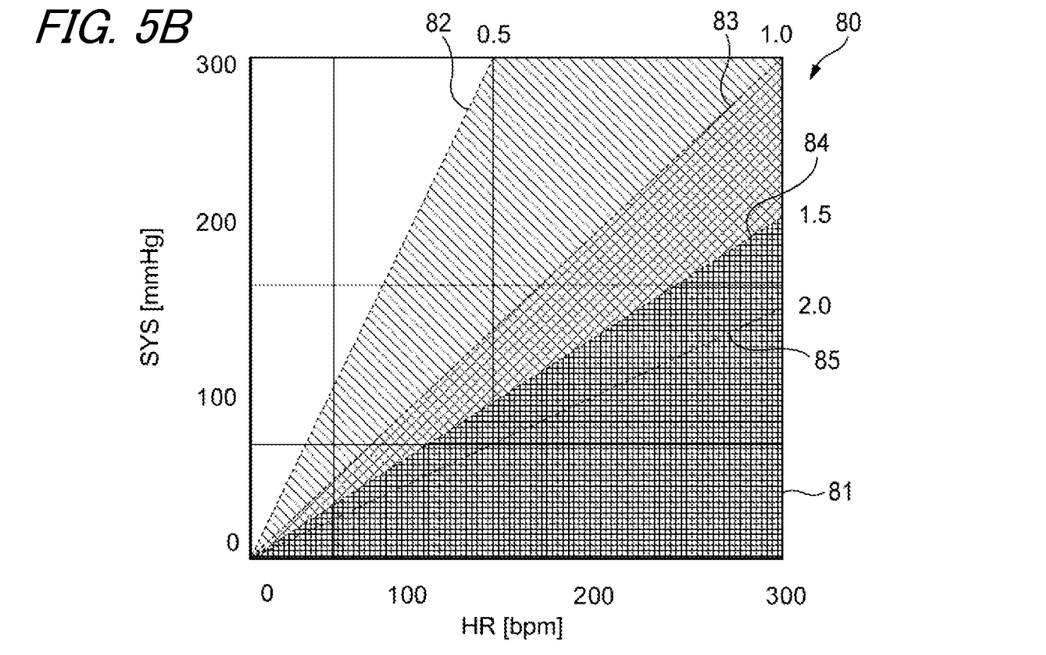

A plurality of types of detection states based on a relationship among measured values of a plurality of parameters do not always need to be defined on the basis of threshold values set on the respective parameters. As shown in FIG. 5B, the detection states can also be partitioned in accordance with a ratio among measured values of the selected parameters.

The drawing shows an example of a status setting screen 80 to be displayed on the display section 14 when a cardiac rate and blood pressure in a contraction stage are selected as a plurality of parameters. Four threshold value setting lines 82 to 85 that extend from the point of origin at predetermined gradients are displayed on a coordinate plane 81 formed from a horizontal axis assigned to the cardiac rate and a vertical axis assigned to the blood pressure in a contraction stage. Gradients of the respective threshold value setting liens correspond to a ratio of a measured value of the cardiac rate to a measured value of the blood pressure in the contraction stage. Domains assigned to a total of five detection states are defined on the coordinate plane 81 by means of the threshold value setting lines 82 to 85 corresponding to ratio values of 0.5, 1.0, 1.5, and 2.0. As in the case with the embodiment, the alarm statuses are assigned to the respective domains and displayed in predetermined colors.

Figure 6:
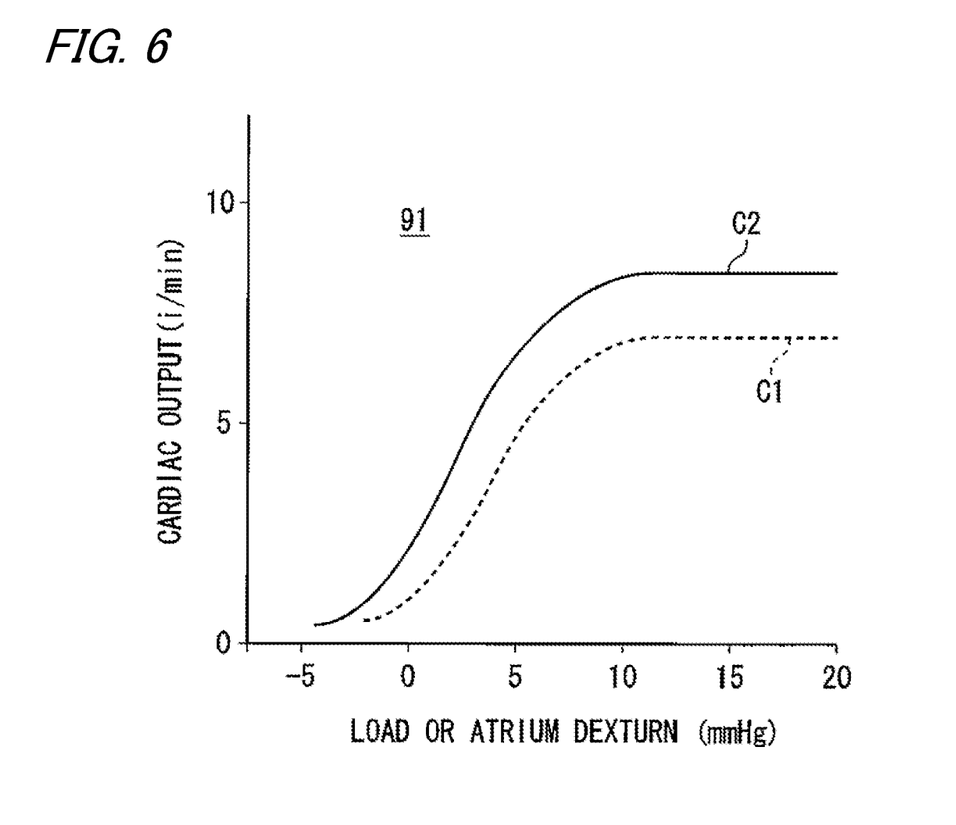
FIG. 6 is a diagram showing yet another example of the alarm status setting screen to be displayed in the display section of the monitor.

A plurality of types of detection states based on a relationship among measured values of a plurality of parameters can also be partitioned on the basis of an oxygen dissociation curve or a relationship curve among measured values like a heart function curve shown in FIG. 6. In the embodiment, domains assigned to a plurality of detection states are defined on a coordinate plane 91 by means of a heart function curve. Alarm statuses of high priority level are assigned to domains located below a curve C1. Alarm statuses of middle or low priority level are assigned to domains located between curves C1 and C2. The domains are divided by color as in the case with the embodiment, and the domains are omitted from FIG. 6.

Parameters showing a health state of the living body 20 acquired by the measurement section 11 are not limited to two types. Three different types of parameters can also be selected, and a coordinate space formed from coordinate axes assigned to the respective parameters can also be displayed on the display section 14. In this case, the coordinate space is divided into a plurality of domains on the basis of a relationship among measured values of the three types of parameters, and alarm statuses can be assigned to the respective domains. Further, at least one index showing the measured value can be displayed in the coordinate space.

Assignment of the alarm statuses always needs to be performed by use of an orthogonal coordinate system. A relationship between measured values of a plurality of parameters is classified according to a plurality of types of detection states. If any of the plurality of types of alarm statuses can be assigned to the plurality of types of detection states, an appropriate coordinate system and an appropriate display mode can be adopted.

So long as the annunciation section 16 can output the alarm corresponding to the assigned alarm status, the coordinate plane 41 used in setting statuses do not always need to be displayed on the display section 14 during measurement of parameters of the living body.

What is claimed is:

1. A monitor comprising:
    a processor having a plurality of sections configured to execute steps of a control program;
    a storage memory medium configured to store the steps of the control program;
    a measurement section configured to acquire measured values of a plurality of parameters indicating a health state of a living body;
    a classification setting section configured to classify a relationship among the measured values of the plurality of parameters into a plurality of types of detection states;
    a status setting section including a command input section through which a user respectively assigns any of a plurality of types of alarm statuses to the plurality of types of detection states arbitrarily;
    a state specifying section configured to specify one of the plurality of types of detection states on the basis of the measured values acquired by the measurement section;
    an annunciation section configured to output an alarm corresponding to the alarm status assigned to the specified detection state;
    a display section; and
    a display control section configured to cause the display section to display a coordinate plane defined by a vertical axis and a horizontal axis, the coordinate plane being assigned to the plurality of parameters, wherein
    the plurality of types of detection states correspond to domains on the coordinate plane,
    the coordinate plane includes a plurality of vertical threshold setting lines that extend parallel to the vertical axis, are straight lines and are set for the plurality of parameters, and a plurality of horizontal threshold setting lines that extend parallel to the horizontal axis, are straight lines and are set for the plurality of parameters,
    the vertical threshold setting lines and the horizontal threshold setting lines intersect to define the domains on the coordinate plane,
    the plurality of types of alarm statuses includes a high priority (Crisis), a middle priority (Warning), a low priority (Advisory), and a non-alarm status, and
    the high priority (Crisis) is assigned to a part of the domains defined by the vertical axis, one of the vertical threshold setting lines that is closest to the vertical axis, and the horizontal threshold setting lines, or a part of the domains defined by the horizontal axis, one of the horizontal threshold setting lines that is closest to the horizontal axis, and the vertical threshold setting lines.

2. The monitor according to claim 1, wherein assignment of the alarm statuses is carried out by use of the coordinate plane.

3. The monitor according to claim 1, wherein the display control section is configured to display at least one of indices corresponding to the measured values in the coordinate system.

4. The monitor according to claim 1, wherein the display control section is configured to change at least one of a color, brightness, and a shape of an index according to a time when the measurement section acquired the measured value.

5. The monitor according to claim 3, further comprising a data specifying section configured to specify at least one of the indices, wherein the display control section is configured to cause the display section to display a moment-to-moment change in the measured value so as to include a time when the measurement section acquired the measured value corresponding to an index specified by the data specifying section.

6. The monitor according to claim 1, wherein requirements for demarcation among the plurality of types of classified detection states are made variable by the classification setting section.

7. The monitor according to claim 1, wherein the plurality of parameters can be selected from a parameter group including a cardiac rate, a frequency of pulse, arterial oxygen saturation, oxyecoia partial pressure, carbon dioxide partial pressure, a concentration of carbon dioxide at end-expiration, a concentration of inspired carbon dioxide, blood pressure, a breathing rate, brain pressure, body heat, an ST value, Apnea (a period of cessation of respiration), FiO2 (an expiratory oxygen concentration), an amount of circulating blood, a cardiac output, a BIS value (a bispectral index), a concentration of anesthetic gas, a vent airflow, an expiratory airflow, a SV (single stroke volume), SVV (a coefficient of fluctuation in single stroke volume), PPV (a coefficient of fluctuation in pulse pressure), SPV (coefficient of fluctuation in blood pressure in contraction stage), and PI (pulse rate).

8. A monitor comprising:
a processor having a plurality of sections configured to execute steps of a control program;
a storage memory medium configured to store the steps of the control program;
a measurement section configured to acquire a measured value of a first parameter and a measured value of a second parameter that represent a health state of a living body;
a classification setting section configured to classify a relationship between a measured value of the first parameter and a measured value of the second parameter into a plurality of types of detection states;
a status setting section including a command input section through which a user assigns any of the plurality of types of alarm statuses respectively to the plurality of types of detection states arbitrarily;
a state specifying section configured to specify one of the plurality of types of detection states according to the measured value acquired by the measurement section;
an annunciation section configured to output an alarm corresponding to an alarm status assigned to the specified detection state;
a display section; and
a display control section configured to cause the display section to display a coordinate plane defined by a vertical axis and a horizontal axis assigned to the first parameter and the second parameter, wherein assignment of the alarm statuses is configured to be carried out by use of the coordinate plane, wherein
the plurality of types of detection states correspond to domains on the coordinate plane,
the coordinate plane includes a plurality of vertical threshold setting lines that extend parallel to the vertical axis, are straight lines and are set for the plurality of parameters, and a plurality of horizontal threshold setting lines that extend parallel to the horizontal axis, are straight lines and are set for the plurality of parameters,
the vertical threshold setting lines and the horizontal threshold setting lines intersect to define the domains on the coordinate plane,
the plurality of types of alarm statuses includes a high priority (Crisis), a middle priority (Warning), a low priority (Advisory), and a non-alarm status, and
the high priority is assigned to a part of the domains defined by the vertical axis, one of the vertical threshold setting lines that is closest to the vertical axis, and the horizontal threshold setting lines, or a part of the domains defined by the horizontal axis, one of the horizontal threshold setting lines that is closest to the horizontal axis, and the vertical threshold setting lines.

9. The monitor according to claim 2, wherein the display control section is configured to cause the display section to display the vertical threshold setting lines and the horizontal threshold setting lines on the coordinate plane, and
one of the domains is displayed in a different aspect relative to other domains.

10. The monitor according to claim 8, wherein
the display control section is configured to cause the display section to display the vertical threshold setting lines and the horizontal threshold setting lines on the coordinate plane, and
one of the domains is displayed in a different aspect relative to other domains.

11. A monitor comprising:
a processor having a plurality of sections configured to execute steps of a control program;
a storage memory medium configured to store the steps of the control program;
a measurement section configured to acquire measured values of a plurality of parameters indicating a health state of a living body;
a classification setting section configured to classify a relationship among the measured values of the plurality of parameters into a plurality of types of detection states;
a status setting section including a command input section through which a user respectively assigns any of a plurality of types of alarm statuses to the plurality of types of detection states in accordance with the health state of the living body;
a state specifying section configured to specify one of the plurality of types of detection states on the basis of the measured values acquired by the measurement section;
an annunciation section configured to output an alarm corresponding to the alarm status assigned to the specified detection state;
a display section; and
a display control section configured to cause the display section to display a coordinate plane defined by a vertical axis and a horizontal axis, the coordinate plane being assigned to the plurality of parameters, wherein
the plurality of types of detection states correspond to domains on the coordinate plane,
the coordinate plane includes a plurality of vertical threshold setting lines that extend parallel to the vertical axis, are straight lines and are set for the plurality of parameters, and a plurality of horizontal threshold setting lines that extend parallel to the horizontal axis, are straight lines and are set for the plurality of parameters,
the vertical threshold setting lines and the horizontal threshold setting lines intersect to define the domains on the coordinate plane, the plurality of types of alarm statuses includes a high priority (Crisis), a middle priority (Warning), a low priority (Advisory), and a non-alarm status, and the high priority (Crisis) is assigned to a part of the domains defined by the vertical axis, one of the vertical threshold setting lines that is closest to the vertical axis, and the horizontal threshold setting lines, or a part of the domains defined by the horizontal axis, one of the horizontal threshold setting lines that is closest to the horizontal axis, and the vertical threshold setting lines.

* * * * *